United States Patent [19]

Ligon et al.

[11] Patent Number: 5,281,397

[45] Date of Patent: * Jan. 25, 1994

[54] ADJUSTABLE OPEN-SPLIT INTERFACE FOR A GAS CHROMATOGRAPH AND A MASS SPECTROMETER

[75] Inventors: Woodfin V. Ligon; Hans Grade, both of Schenectady, N.Y.

[73] Assignee: General Electric Company, Schenectady, N.Y.

[*] Notice: The portion of the term of this patent subsequent to Apr. 28, 2009 has been disclaimed.

[21] Appl. No.: 78,991

[22] Filed: Jun. 11, 1993

Related U.S. Application Data

[63] Continuation of Ser. No. 669,556, Mar. 14, 1991, abandoned.

[51] Int. Cl.$^5$ .......................................... G01N 30/02
[52] U.S. Cl. .................................. 422/89; 422/83; 422/103; 73/23.37; 73/23.42; 73/864.81; 250/288; 436/161; 96/106
[58] Field of Search ............... 436/161; 422/83, 89, 422/103; 55/67, 386; 73/23.41, 23.37, 23.42, 864.85, 864.81; 250/288, 288 A

[56] References Cited

U.S. PATENT DOCUMENTS

| | | | |
|---|---|---|---|
| 3,860,393 | 1/1975 | Campen, Jr. | 422/89 |
| 3,936,374 | 2/1976 | Bradley et al. | 55/67 |
| 4,654,052 | 3/1987 | Sharp | 422/70 |
| 4,662,914 | 5/1987 | Hansen et al. | 422/70 |
| 4,713,963 | 12/1987 | Sharp | 73/23.37 |
| 4,842,701 | 6/1989 | Smith et al. | 436/173 |
| 5,108,468 | 4/1992 | Ligon, Jr. | 55/208 |

OTHER PUBLICATIONS

Multidimensional Gas Chromatography: Techniques and Applications, Woodfin V. Ligon, Jr. —GE Corp. Reseaarch & Development pp. 55-85 in Gas Chromatography: Biochemical, Biomedical and Clinical Applications Ray E. Clement, ed. John Wiley & Sons Inc. 1990.
Journal of High Resolution Chromatography–"A Versatile Interface Modification for GC/MS on Benchtop Instruments"—L. Hathcock et al. (1990) pp. 656≧658.
"Open Split Interface for Capillary Gas Chromatography/Mass Spectrometry, " R. F. Arrendale et al. (1984) pp. 1533-1537 Anal. Chem. vol. 56 No. 8.
Journal of Chromatography, 112 (1975)—"Special Techniques in the Combination of Gas Chromatography and Mass Spectrometry, " D. Henneberg et al. pp. 343-351.
Anal. Chem. (1988) —vol. 60, No. 19 pp. 2172-2174—"Cross-Bore Open-Split Interface for Gas Chromatography Coupled with Mass Spectrometry and Infrared Spectrometry, " S. Bourne and William R. Croasmun.
Anal. Chem. vol. 50, No. 14, Dec. 1978—"All-Glass Open-Split Interface for Gas Chromatography-Mass Spectrometry," Hans-Jurgen Stan and Bernd Abraham—pp. 2161-2164.
Journal of High Resolution Chromatography & Chromatography Communications—"Fused Silica Open-Split GC/MS Interface," J. F. Pankow and L. M. Isabelle (1987) pp. 617-619.
Journal of Chromatography, 450(1988)—Open Split Interfaces in Capillary Gas Chromatography-Mass Spectrometry-Yield and Quantitative Aspects, N. W. Davies pp. 388-393.
A Universal, Inexpensive Fused-Silica Interface for Gas Chromatography–Mass Spectrometry, Robert T. Rosen and Thomas G. Hartman.

*Primary Examiner*—James C. Housel
*Assistant Examiner*—Jan M. Ludlow
*Attorney, Agent, or Firm*—William H. Pittman

[57] ABSTRACT

An apparatus and a method providing an open-split interface between a gas chromatograph and a mass spectrometer for delivering a substantially solvent free sample material from the gas chromatograph to the mass spectrometer. The apparatus has a junction having an inlet to receive a gas chromatograph effluent. An inert auxiliary fluid such as helium supplied through a port is used to scavenge the solvent rich effluent to atmosphere. A transfer member disposed partially within the junction is initially positioned at a first position to accomplish the aforementioned scavenging action. The transfer member is then repositioned to a second position to direct the substantially solvent free sample to the mass spectrometer for a qualitative and a quantitative analysis.

16 Claims, 8 Drawing Sheets

ADJUSTABLE OPEN-SPLIT INTERFACE FOR A GAS CHROMATOGRAPH AND A MASS SPECTROMETER

This application is a continuation of application Ser. No. 07/669,556, filed Mar. 14, 1991, now abandoned.

FIELD OF THE INVENTION

The present invention generally relates to an interface used for coupling a gas chromatograph to a mass spectrometer, and more particularly concerns an open-split interface used for providing a substantially solvent free sample material from a gas chromatograph to a mass spectrometer.

BACKGROUND OF THE INVENTION

The basis of chromatography is the separation of components of a sample owing to their differences in solubility or in adsorption in a stationary bed of a material (either liquid or solid). When the sample (moving phase) is a gas, the technique is termed either gas-solid or gas-liquid chromatography, depending on whether the stationary phase is a solid or a liquid. In gas chromatography, a sample is introduced into a carrier gas as a vapor which flows through a chromatographic system. Upon separation by the stationary phase, the sample components travel through the system at different speeds thereby entering a detecting device, attached to the system, at different times. As a result, individual components that are present in the sample may be identified by the detecting device.

A chromatograph such as a gas chromatograph, sometimes hereinafter GC, is an analytical instrument which can separate a gaseous mixture into its various constituent parts. A detecting device such as a mass spectrometer, sometimes hereinafter MS, is an analytical instrument which can qualitatively and quantitatively analyze a gaseous sample to determine its molecular structure. Both gas chromatographs and mass spectrometers have been around for a relatively long time. It has long been recognized that a powerful analytical tool could be obtained by coupling these two instruments. However, combination GC/MS instruments are relatively recent innovations, and continuing research and development is directed towards improving the interface between the gas chromatograph and the mass spectrometer portions of GC/MS instruments.

A typical GC/MS interface includes a tubular transfer line having one end coupled to the output of the gas chromatograph and having its other end extending into a vacuum chamber of the mass spectrometer. An ion source of the mass spectrometer is used to ionize the effluent from the transfer line, and a mass filter of the mass spectrometer is used to filter the ionized components of the gas according to mass. An ion detector within the vacuum chamber of the mass spectrometer detects ions filtered through the mass filter. Finally, a recorded output signal of the detector is studied to determine the chemical structure of the gas sample.

However, gas chromatographs generally operate at atmospheric pressure while mass spectrometers operate at greatly reduced pressures, generally at about $1 \times 10^{-5}$ Torr. To balance such significant differences in pressures between the two devices, the GC/MS interface must provide some means to reduce the pressure of a sample gas leaving the gas chromatograph prior to its introduction into the mass spectrometer. Furthermore, since gas chromatographs operate by sweeping small amounts of sample gas through the GC column, at high volumetric rates of the carrier gas, some means must be found to enrich the concentration of the sample gas relative to the carrier gas before the gas mixture reaches the mass spectrometer. Failure to execute the enrichment step reduces the sensitivity of the mass spectrometer.

Since the gas chromatograph separates the various components of the sample gas or a sample material, the composition of the gas leaving the chromatograph varies with time. Because of the continually changing composition of the gas effluent, any mass spectrometer designed for use with a gas chromatograph must be capable of sweeping rapidly across the mass spectrum, for a swift analysis of the changing composition of the GC effluent.

A wide variety of approaches for interfacing gas chromatographs to mass spectrometers have been tried. The most common approach is a direct connection between the two by means of a capillary tube. The advantage of this type interface is its mechanical stability and the consequent ease with which it can be handled, especially when the chromatographic columns are not changed frequently. There are, however, a wide variety of disadvantages to this method. The major disadvantage of such a capillary restriction is that the sample material, including the solvent, elutes directly into the mass spectrometer source, thereby affecting the sensitivity of the MS. Additionally changing of the GC columns is a laborious and time consuming process as the mass spectrometer vacuum system has to be vented with each GC column change. Another drawback is that all of the gas effluent coming from the gas chromatograph is delivered to the mass spectrometer, thereby potentially overloading the mass spectrometer vacuum system. Thus the mass spectrometers normally designed to accept samples only in nanogram quantities, can be exposed to sample quantities in excess of milligrams. Such an extreme exposure to large amounts of elements causes contamination of the ion source, analyzer and vacuum system of the mass spectrometer, thereby increasing its maintenance cost and reducing the life of filaments used in the variable energy ion source of mass spectrometer.

A direct coupling of the GC to the MS also has an effect on the efficiency of the gas chromatographic separation. By directly coupling the GC to the MS the high vacuum of the mass spectrometer affects the GC column flow rates which results in shifting the GC retention times.

Another common alternative is the so called open-split interface. In its simplest form, one end of an interfacing capillary tube usually made of fused silica is used to provide a flow restriction into the mass spectrometer's GC inlet. The other end of the interfacing capillary tube is telescoped into or placed near the outlet of the GC capillary column. By adjusting the length and the inside diameter of the interfacing capillary tube, a natural vacuum induced flow is maintained to the MS without any permanent or elaborate physical connections between the GC and the interfacing capillary tube. Such an open-split interface has several advantages. The GC column is exposed to atmospheric pressure at its outlet, because it is not sealably connected to the MS. As a result the GC column is not affected by the low pressure of the MS. Secondly, when the aforementioned capillary tube is used as a restrictor, it has been shown that there is virtually no degradation of the chromatographic resolution. Thirdly, if the interfacing capillary tube is held at a constant temperature, by jacketing it in a chamber maintained at a constant temperature, the pressure to which the ion source of the MS is exposed, stays constant even if the GC oven temperature is profiled. Finally, if an accidental breakage of the GC column occurs, such an incident has no effect on the integrity of the MS vacuum.

Even though the aforementioned open-split capillary tube interface overcomes many of the problems associated with the GC/MS interface, it is woefully inadequate in addressing the major problem of solvent diversion which has major impact on the sensitivity and the functionality of the MS. The solvent diversion problem has been partially addressed by enclosing the open-split capillary interface in an evacuated enclosure or an enclosure flooded with an inert fluid, such as helium. A large volume of the inert gas is swept through the interface at the start of the process. Substantially large inert gas flow rates are necessary to flush away the solvent prior to its entry into the MS ion source. However, due to small internal volume of the interface, such large inert gas flow rates result in increasing the pressure within the interface to above the atmospheric pressure, thus increasing the GC retention times and the ion source pressure within the MS. As a result the ion source conditions within the MS may be adversely affected.

The gas chromatographs are also used in multiple stages to separate constituents of a component of the sample that may not be separated by a single stage GC column. Such a technique of separation, called multidimensional gas chromatography, utilizes more than one chromatographic column. Such high resolution multidimensional gas chromatographs (hereinafter MGC) generally have GC columns with different liquid phases. When a desired component of the sample is at a "peak" in the first stage it is switched to the second column for further separation of the component into its individual constituents.

The major problem faced by the multidimensional chromatography is a lack of a reliable switching scheme that operates at elevated temperatures without affecting the degree of resolution. Several switching schemes have been in use. However these schemes are cumbersome to operate and are mechanically complex. For a general summary, reference is made to Ligon, W., Multidimensional Gas Chromatography: Techniques and Applications, Chapter 3, pages 55-85 of Gas Chromatography: Biochemical, Biomedical and Clinical Applications, edited by Clement, R., ISBN: 0-471-01048-0, 1990 John Wiley & Sons, Inc., incorporated herein by reference. The present invention addresses the switching problems of the MGCs by using the open-split interfaces of the present invention as a switching system.

SUMMARY OF THE INVENTION

In the present invention the aforementioned problems are solved through a method and an apparatus for interfacing at least one gas chromatograph with a detecting device comprising a junction means having at least one inlet for receiving a chromatograph effluent, a supply means for introducing an inert auxiliary fluid within the junction means, an aperture means for controlling fluid pressure within the junction means, at least one outlet for conveying a mixture to the detecting device, and at least one transfer member disposed partially within the junction means, the member being selectively positionable between a first position and a second position wherein when in the first position the effluent is directed to the aperture means and when in the second position the effluent is directed to the outlet.

The present invention is also directed to an analytical apparatus comprising at least one gas chromatograph further comprising a chromatographic column having a chromatograph carrier fluid inlet and a chromatograph effluent outlet, an injector port for introducing a sample through the chromatographic column, a detecting device, an interface for coupling the chromatograph with the detecting device, the interface further comprising a junction means having at least one inlet for receiving a chromatograph effluent, a supplying means for introducing an inert auxiliary fluid within the junction means, an aperture means for controlling fluid pressure within the junction means, at least one outlet for conveying a mixture to the detecting device, at least one transfer member disposed partially within the junction means, the member being selectively positionable between a first position and a second position, a heated chamber for enclosing and maintaining the chromatograph and the interface at a desired temperature, and a heating means to preheat the inert fluid to a required temperature before entry of the inert fluid into the junction means.

The present invention is further directed to a method of providing a sample material from at least one gas chromatograph to a detecting device comprising supplying an inert auxiliary fluid from a supply means to an interface connected between the gas chromatograph and the detecting device, positioning a transfer member disposed partially within a junction means of the interface to a first position whereby the inert fluid is directed to an aperture means of the interface, introducing a gas effluent containing a solvent from at least one of the gas chromatographs through at least one inlet of the junction means, entraining a substantial quantity of the solvent into the inert auxiliary fluid, diverting the substantial quantity of the solvent to the atmosphere through the aperture means of the interface, repositioning the transfer member to a second position for directing a mixture to an outlet of the interface, and introducing the mixture into the detecting device.

Other advantages of the invention will become apparent upon reading the following detailed description and appended claims, and upon reference to the accompanying drawings.

BRIEF DESCRIPTION OF THE DRAWINGS

For a more complete understanding of this invention reference should now be had to the embodiments illustrated in greater detail in the accompanying drawings and described below by way of examples of the invention.

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

DETAILED DESCRIPTION OF THE INVENTION

Figure 1:
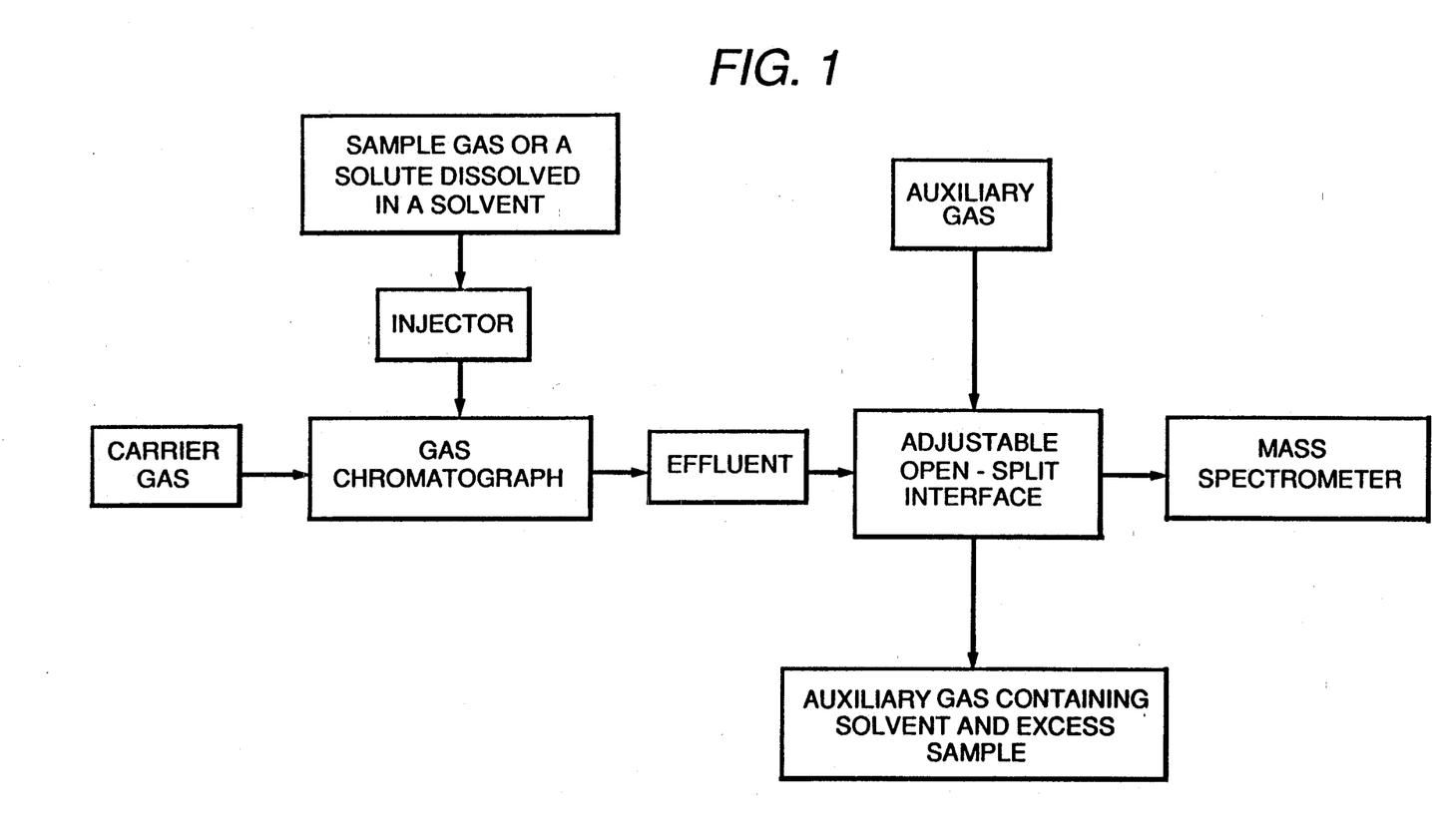
FIG. 1 is a block diagram depicting the major components of the apparatus of the present invention.

Turning to FIG. 1 there is shown a block diagram, generally pointing out the path of travel of the sample material being analyzed by the apparatus of the present invention. The material to be analyzed is initially isolated in the gas chromatograph. Gas chromatographic separation involves the process of using a carrier gas to force a sample gas through a column containing a separation medium. Typically such a column is made from a fused silica tubing having its inner diameter coated with a polymeric material (stationary liquid phase) such as polydimethylsiloxane. Generally the inner diameter of the tubing is about 0.25 to about 0.32 millimeters. The carrier gas is generally an inert gas, such as helium. Once the sample gas has been "carried" through the chromatographic column by the carrier gas, the function of the carrier gas has been served and its presence in high concentration impedes identification of the various sample gas components by a detecting device such as a mass spectrometer.

Alternatively, a sample may be dissolved in a solvent and then injected by an injector into the gas chromatographic column wherein dissolved solute is "carried" by the GC carrier gas, such as helium, to the mass spectrometer. The function of the aforementioned solvent is only to facilitate efficient transport of the sample to the GC, however, its presence in the ionization block of the MS severely effects the sensitivity of the MS.

The adjustable open-split interface of the present invention allows efficient removal of the solvent from the sample solute, thereby providing a substantially solvent free solute into the mass spectrometer.

The gas chromatograph may be of any conventional design, such as a Hewlett-Packard Model 5890 GC.

The solute substantially free from the solvent is ionized, filtered and analyzed by any conventional mass spectrometer such as a JEOL (Japanese Electronics Optical Laboratories) Model SX102.

The adjustable open-split interface may be also used in the MGC used during a high resolution gas chromatography.

Figure 2:
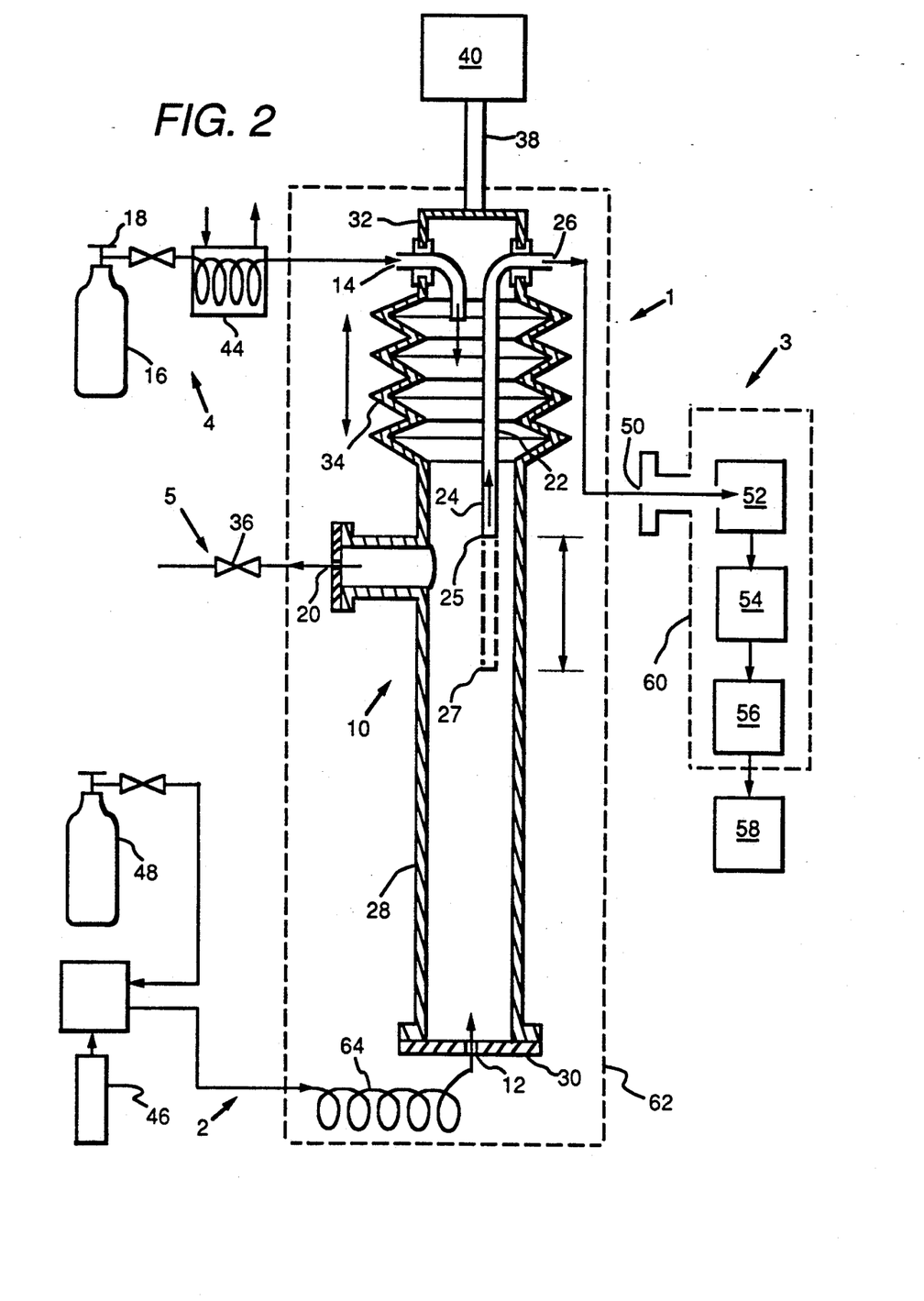
FIG. 2 is a view of an apparatus of the preferred embodiment.
Figure 2A:
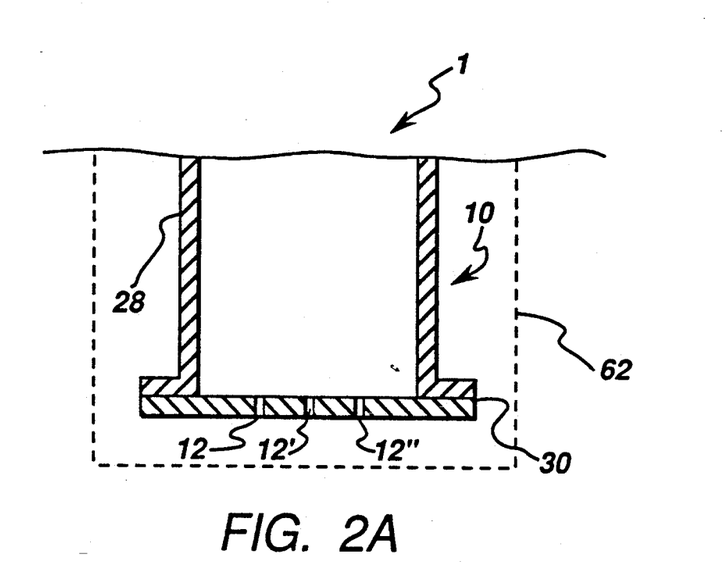
FIG. 2A is a partial view of the apparatus of the preferred embodiment showing additional inlets for connecting a plurality of chromatographs.

Turning now to FIG. 2, there is shown an apparatus of the preferred embodiment of the invention. The adjustable open-split interface generally indicated by numeral 1, connects at least one gas chromatograph 2 with a detecting device 3, typically a mass spectrometer. Interface 1 includes a junction means, generally indicated by numeral 10, comprising a hollow close ended conduit 28 having a first end 30 and a second end 32. Preferably an inert material such as a glass lined stainless steel is used in the fabrication of junction means 10 so that it has a negligible effect on the solute sample material being analyzed by the detecting device 3. In the preferred embodiment of the present invention, junction means 10 was fabricated from a glass lined tubing supplied by SGE (Scientific Glass Engineering) Company, Austin, Tex. However to those skilled in the art, alternatives to the aforementioned product will be apparent. An inlet 12, provided near first end 30 of conduit 28, is connected through a compression fitting such as a Swagelok ® fitting to chromatograph 2. Junction means 10 may be provided additional inlets 12' and 12", as shown in FIG. 2A, for connecting additional gas chromatographs.

A port 14, provided near second end 32 of conduit 28, is connected to supply means of an inert auxiliary fluid supply, generally indicated by a numeral 4. Preferably an inert auxiliary fluid introduced from vessel 16 through port 14 is the same as a GC carrier gas supplied from vessel 48, such as helium. An inert auxiliary fluid regulating means 18 are used to control the flow of the inert auxiliary fluid from vessel 16. A heating means 44, may be interposed between an inert auxiliary fluid regulating means 18 and port 14 of junction means 10, for controlling the temperature of the inert auxiliary fluid, before its entry into junction means 10. The source of heat within heating means 44 may be provided, for example, by electrically heated resistance coils. However, it will be obvious to those skilled in the art to use some other means for heating the inert auxiliary fluid to a desired temperature.

Interface 1 is further provided with an aperture means, generally indicated by numeral 5. Aperture means 5 connected to an exhaust port 20, preferably located between first end 30 and second end 32 of junction means 10, permits controlling of pressure within junction means 10 by a regulator 36 located in an exhaust line of aperture means 5 open to the atmosphere. It is contemplated that, if required, the exhaust line may be connected to a vacuum system, not shown, to expose junction means 10 to less than atmospheric pressure.

At least one outlet of interface 1 is provided by at least one hollow elongated transfer member 22 having outlet 26 at one end and an intake 24 at the other end. The outlet is provided for conveying a mixture from interface 1 to detecting device 3. The mixture comprises the inert auxiliary fluid, the effluent from the GC or a combination thereof. The transfer member 22 coaxially disposed within conduit 28, has a portion of it, nearer to outlet 26, projecting outwardly from near second end 32 of conduit 28. Transfer member 22 is preferably a fused silica capillary tube having an internal diameter of about 0.1 to about 0.2 millimeters. However, it is contemplated that those skilled in the art may utilize some other types of capillary tubes. The internal diameter of the transfer member 22 should be adjusted to maintain a level of vacuum at which detecting device 3 operates.

Second end 32 of conduit 28 is provided with a bellows 34, having a closed end. Transfer member 22 enters conduit 28 from near a crown of bellows 34 and it is affixed to the crown of bellows 34. Transfer member 22 is provided a reciprocal motion by compression and expansion of bellows 34. As a result of such a reciprocal motion, intake 24 of transfer member 22 may be selectively positioned between a first position 25 and a second position 27, shown by dotted lines in FIG. 2. When transfer member 22 is in first position 25 the GC effluent is directed to aperture means 5 and when transfer member 22 is in the second position 27 the GC effluent is directed to outlet 26.

Junction means 10 and a chromatographic column 64 of GC 2 are preferably enclosed within a heated chamber 62 maintained at a desired temperature. Junction means 10 may be provided a plurality of inlets for connecting more than one GC chromatograph to interface 1. Junction means 10 may be also provided with at least one entry port for injecting chemical reagents into the GC effluent entering junction means 10 for a post column derivatization. The post column derivatization is a verification step used for establishing identity of the component present in the GC effluent. A chemical reaction is carried out between the separated component exiting from the GC column and the chemical reagent before the reacted component enters the mass spectrometer. For example, deuterium oxide may be used as the chemical reagent to establish identity of a hydroxyl group.

A driving means 40, preferably powered by electromechanical means such as a solenoid, is connected to a driver end of an actuating lever 38. The driven end of actuating lever 38 is affixed to the crown of bellows 34. Preferably the energization of driving means 40 is controlled through a software program executed by a computer. However, any other conventional driving means such as manually applied power are also contemplated.

Junction means 10 is connected to detecting device 3, by coupling outlet 26 to an input orifice 50 of detecting device 3. Types of detecting devices suitable for the present invention are a mass spectrometer, flame ionization detector, photoionization detector, electron capture detector, radiometric detector, thermal conductivity detector, flame photometric detector, nitrogen phosphorus detector (FID type), thermionic ionization detector, infrared spectrophotometric detector, atomic absorption spectrometric detector, helium ionization detector, chemiluminescent nitrogen specific detector, the preferred detecting device being a mass spectrometer. It is noted that while using some of the aforementioned detectors, regulator 36 of aperture means 5 may have to be partially closed to increase pressure within junction means 10 to force the mixture from junction means 10 into detecting device 3. Typically outlet 26 is sealably and flexibly coupled, by means of a flexible tubing, to detecting device 3 to allow freedom of movement to transfer member 22. Preferably a conventional mass spectrometer, shown in FIG. 2, is used as detecting device 3. Such a conventional mass spectrometer comprises a variable energy ion source 52, a mass filter 54, an electron multiplier 56 and an analyzing computer 58. Some of the components of the mass spectrometer such as variable energy ion source 52, mass filter 54 and electron multiplier 56 are enclosed within an evacuated chamber 60. It should be understood that the present invention also contemplates use of any other suitable type of mass spectrometer.

Turning now to the operation of the preferred embodiment as shown in FIG. 2, a sample containing various components is dissolved in a solvent, and then injected through an injector 46 into gas chromatograph 2. The solvent containing the dissolved sample is then carried by the carrier gas. The gas chromatograph effluent exiting from chromatographic column 64 is fed through inlet 12 into open-split interface 1 of the present invention. The inert auxiliary fluid, introduced through port 14 into conduit 28, exits out of aperture 20 to the atmosphere. The pressure of the inert auxiliary fluid within conduit 28 may be controlled by adjusting regulating means 36 of aperture means 5. If so desired, regulating means 36 may be connected to a vacuum source, to draw off the inert auxiliary fluid and the GC effluent. However, it is preferable to exhaust the inert auxiliary fluid at normal atmospheric pressure. As the gas chromatograph effluent enters conduit 28, it is exhausted through exhaust port 20 to the atmosphere, along with the inert auxiliary fluid supplied through port 14. Generally the initial GC effluent flow from the GC column is richer in the solvent, and by exhausting the initial GC effluent flow to atmosphere, the effect of the solvent on the MS is minimized. Before the aforementioned initial GC effluent flow is introduced into conduit 28, intake 24 of transfer member 22 is preferably positioned at first position 25 near exhaust port 20, thereby directing the GC effluent to the atmosphere through exhaust port 20 and aperture means 5.

By energizing driving means 40, bellows 34 may be compressed or expanded for providing a reciprocal motion to transfer member 22. As shown by the dotted lines in FIG. 2, intake 24 of transfer member 22 may be located at either first position 25 or second position 27. When intake 24 of transfer member 22, positioned at first position 25, is repositioned to second position 27, the gas chromatograph effluent is directed through outlet 26 of transfer member 22 to orifice 50 of the detecting device 3. The inner diameter of transfer member 22 has a significant impact on the degree of vacuum within detecting device 3. By keeping the inner diameter of transfer member 22 narrow, for example at less than about 0.2 millimeter, the interface of the present invention supplies the GC effluent to the MS under invariant conditions. By positioning intake 24 at intermediate positions between first position 25 and second position 27, detecting device 3 may be incrementally supplied with the inert auxiliary fluid, the gas chromatograph effluent or a mixture of the two.

When a mass spectrometer is used as detecting device 3, the material within the gas chromatograph effluent entering through orifice 50, is converted into an ion beam by variable energy ion source 52. The aforementioned ion beam then passes through mass filter 54 for selecting ions of a desired mass to charge ratio and for filtering out the remaining nonselected ions. The current, produced by the ion beam of the selected ions, is then provided with a gain by electron multiplier 56. By providing such a gain, the quality of an analysis of the selected ions is significantly improved. Computer 52 then qualitatively and quantitatively analyzes the signals generated by the selected ions for providing the desired analysis of the sample introduced in the GC.

Figure 3:
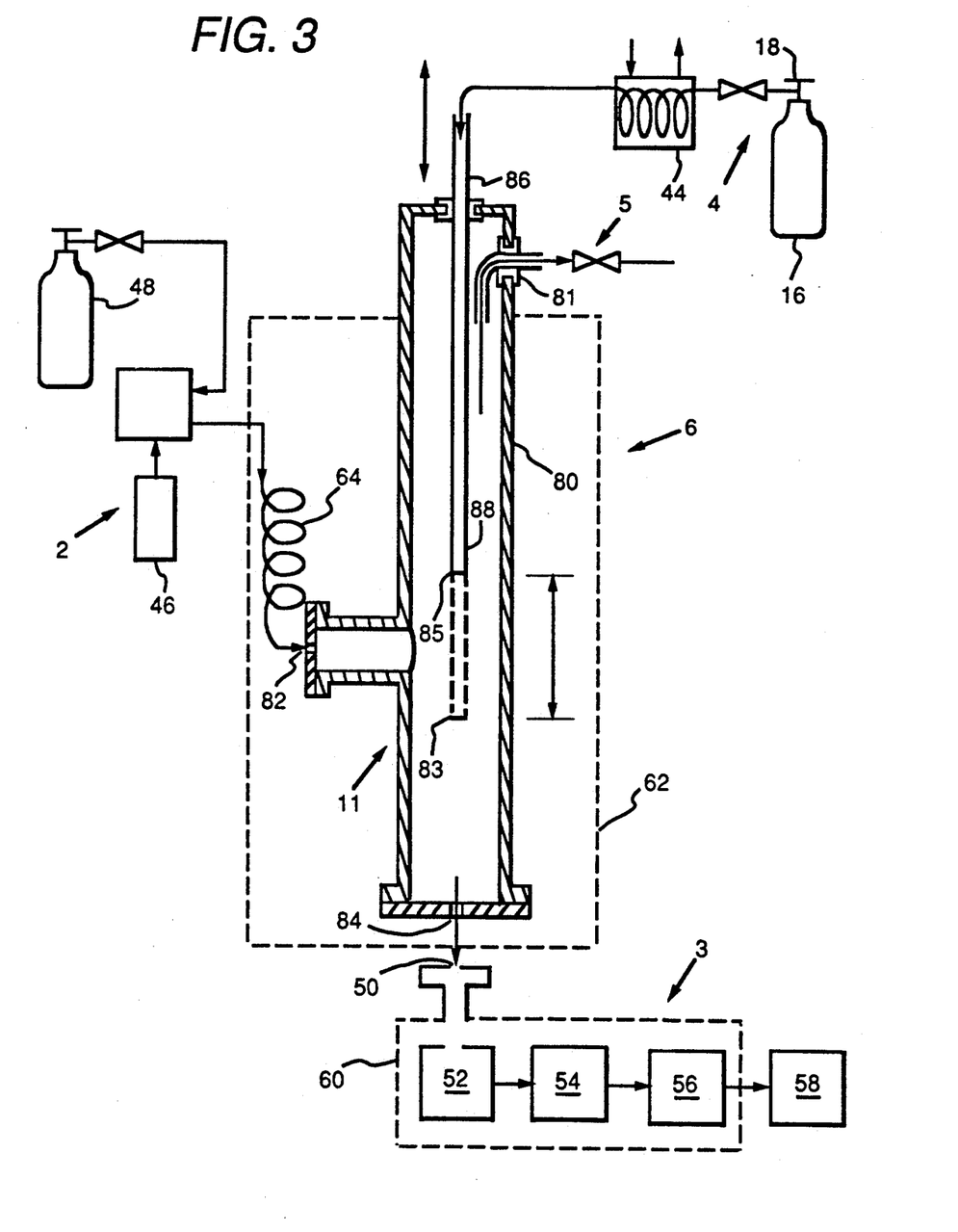
FIG. 3 is a view of an apparatus of another embodiment of the present invention.

FIG. 3 illustrates another embodiment of the present invention showing an adjustable open-split interface, generally indicated by numeral 6. As so far described some of the implements of FIG. 3 are substantially like those of FIG. 2. The two differ primarily in that FIG. 3 provides a different style of an open-split interface than in FIG. 2. All the components substantially same between FIG. 2 and FIG. 3 are represented by same numerals. Interface 6 comprises a junction means, generally indicated by numeral 11.

A manifold 80 of interface 6 having a first end and a second end is provided with an outlet 84 at the first end. Outlet 84 is connected to a conventional detecting device 3, such as a mass spectrometer. An inlet 82 is provided on a side of manifold 80 to admit the effluent from the gas chromatograph generally indicated by numeral 2. An exhaust port 81 located near the second end of manifold 80 is connected to aperture means 5. A hollow coaxially disposed elongated transfer member 86 partially telescopes within manifold 80 and has its exposed end connected to supply means of an auxiliary inert fluid supply, generally indicated by a numeral 4. A supply end 88 of elongated transfer member 86 may be selectively positioned at a first position 83 near the first end of manifold 80 or at a second position 85 near the second end of manifold 80. Transfer member 86 may be directed to first position 83 or to second position 85 by providing it with reciprocal motion through a driving means not shown in FIG. 3. However to those skilled in the art, it will be apparent to use driving means such as an electrically operated solenoid for providing the required reciprocal motion. When transfer member 86 is in first position 83, the GC effluent is directed to aperture means 5 and when transfer member 86 is in second position 85 the GC effluent is directed to outlet 84.

In operation, as shown in FIG. 3, supply end 88 of elongated transfer member 86 is initially positioned at first position 83 and the inert auxiliary fluid is introduced into manifold 80 through supply end 88 of transfer member 86 and allowed to escape to the atmosphere by passing through aperture means 5. When the gas chromatograph effluent is introduced through inlet 82, the initial solvent rich effluent is carried off to the atmosphere by the inert auxiliary fluid. At a desired moment, elongated transfer member 86 is repositioned to second position 85 by the driving means, not shown, thereby moving supply end 88 from near outlet 84 to near inlet 82. Such a displacement of elongated member 86 is shown by the dotted line in FIG. 3. The GC effluent entering through inlet 82 is now urged by auxiliary inert fluid 16 towards outlet 84. The GC effluent is then introduced into detective device 3 through orifice 50 of detecting device 3 connected to outlet 84.

Figure 4:
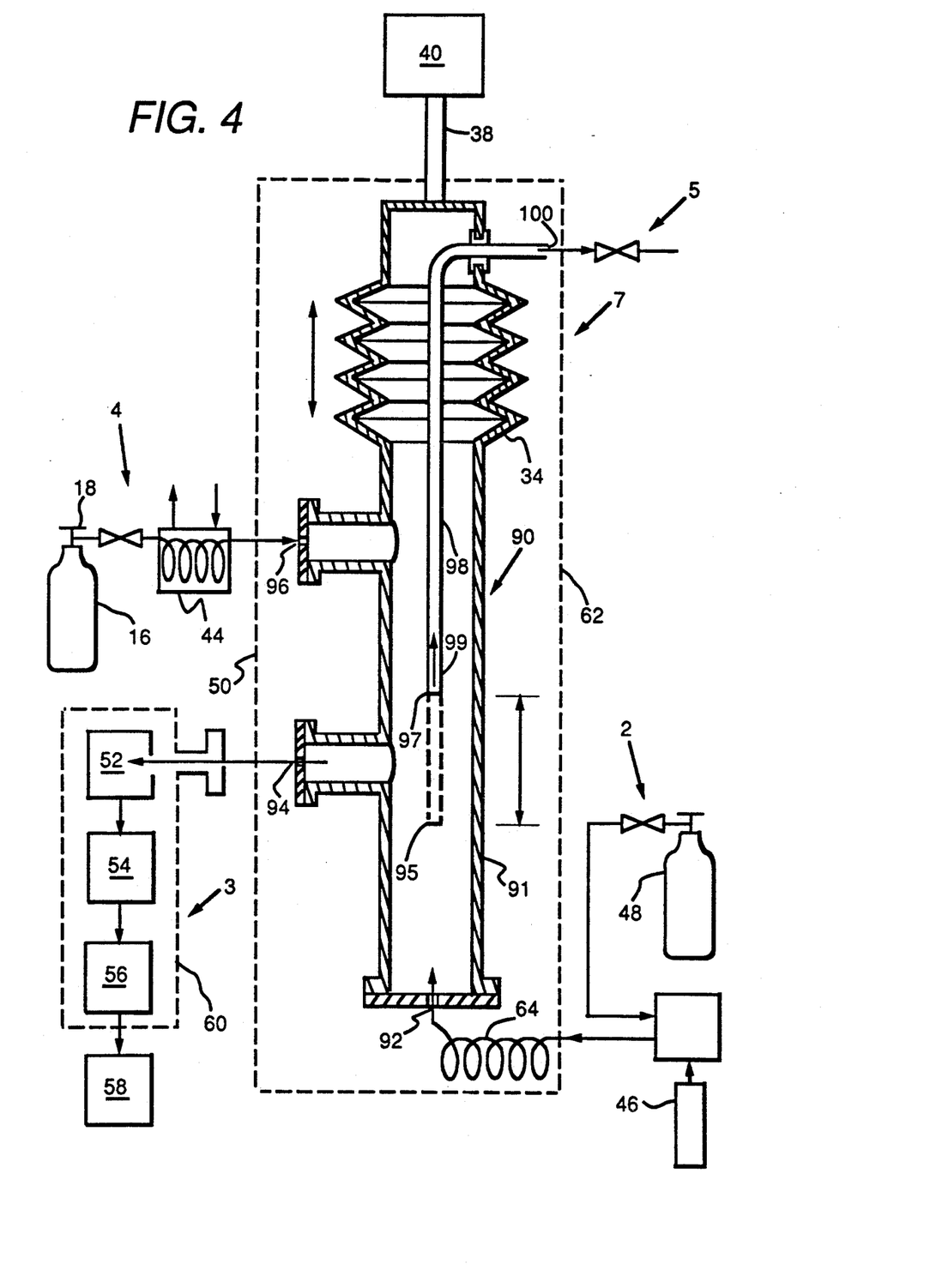
FIG. 4 is a view of an apparatus of yet another embodiment of the present invention.

FIG. 4 illustrates yet another embodiment of the present invention showing an open-split interface, generally indicated by numeral 7. As so far described some of the implements of FIG. 4 are substantially like those of FIG. 2. The two differ primarily in that FIG. 4 provides a different style of an open-split interface than in FIG. 2. All the components substantially same between FIG. 2 and FIG. 4 are represented by same numerals. Interface 7 comprises a junction means, generally indicated by numeral 90 and formed by a close ended conduit 91. An inlet 92 positioned at a first closed end of conduit 91 is connected to the gas chromatograph, generally indicated by numeral 2. A second closed end of conduit 91 is provided a bellows 34 operated by driving means 40 connected through an actuating lever 38 to the crown of bellows 34.

Conduit 91 is further provided with a port 96 preferably positioned near the second closed end of conduit 91 and connected to supply means, generally indicated by numeral 4 for introducing the inert auxiliary fluid within junction means 90. An outlet 94 preferably positioned near the first end of conduit 91 is connected to orifice 50 of detecting device, generally indicated by numeral 3.

At least one coaxially disposed elongated transfer member 98 is partially disposed within conduit 91. Transfer member 98 is further provided an intake end 99 and an exhaust end 100, wherein exhaust end 100 is connected to aperture means, generally indicated by numeral 5. Intake end 99 may be selectively positioned at a first position 95 near inlet 92 or to a second position 97 near outlet 94. Transfer member 98 affixed to bellows 34 may be directed to first position 95 or to second position 97 by providing a reciprocal motion to it through an actuation of bellows 34 by driving means 40. However it will be apparent to those skilled in the art to use some other means of providing the reciprocal motion to transfer member 98. When transfer member 98 is in first position 95, the GC effluent is directed to aperture means 5 and when transfer member 98 is in second position 97 the GC effluent is directed to outlet 94.

In operation, as seen in FIG. 4, intake end 99 of elongated transfer member 98 is initially positioned at first position 95 and the inert auxiliary fluid is introduced into conduit 91 through port 96 and allowed to escape to the atmosphere by passing through aperture means 5 connected to exhaust end 100. When the gas chromatograph effluent is introduced through inlet 92, the initial solvent rich effluent is carried off to atmosphere by the inert auxiliary fluid. At a desired moment, elongated transfer member 98 is repositioned to second position 97 by driving means 40, thereby placing intake end 99 from near inlet 92 to near outlet 94. Such a displacement of elongated member 98 is shown by the dotted line in FIG. 4. The GC effluent entering through inlet 92 is now urged by the inert auxiliary fluid towards outlet 94. The GC effluent is then introduced into detective device 3, for the analysis, through orifice 50 of detecting device 3 connected to outlet 94.

Figure 5:
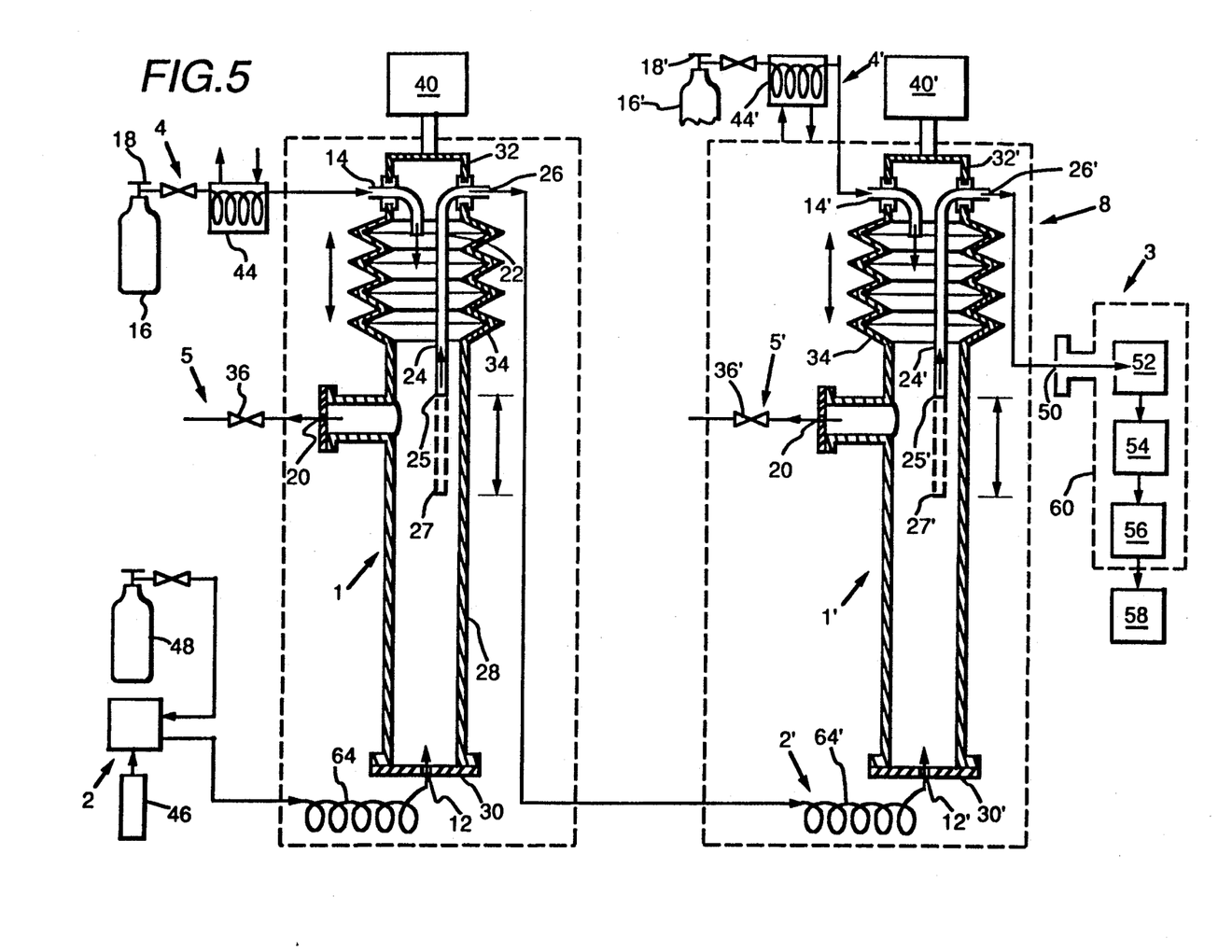
FIG. 5 is a view of an apparatus of still another embodiment of the present invention.

FIG. 5 illustrates another embodiment of the present invention showing an improved multidimensional gas chromatograph, generally indicated by numeral 8. As so far described some of the implement of FIG. 5 are substantially like those of FIG. 2. However FIG. 5 provides the multidimensional gas chromatography apparatus used for significantly improving the power of resolution of a gas chromatograph. All the components substantially the same between FIG. 2 and FIG. 5 are represented by same numerals. Multidimensional gas chromatographs are very useful in separating individual components of sample material having same solubility in a liquid phase of a gas chromatographic column used during chromatography. A desired peak component from the sample separated by a first chromatographic column and containing the individual constituents having same solubility can then be passed through a second gas chromatographic column having a different liquid phase capable of separating the individual constituents further.

Multidimensional gas chromatograph apparatus comprises a series of adjustable open-split interfaces alternately connected to a series of gas chromatographs. FIG. 5 shows a 2-dimensional gas chromatograph apparatus. A first stage of apparatus 8 is a first interface generally indicated by numeral 1 and a second stage of apparatus 8 is a second interface generally indicated by numeral 1'. Inlet 12 of first interface 1 is connected to a first chromatograph generally indicated by a numeral 2. Outlet 26 of first interface 1 is connected to chromatographic column 64, of second gas chromatograph 2'. It should be noted that injector 46 and the carrier gas are only provided to first chromatograph 2. In addition to the carrier gas, the inert auxiliary fluid supplied to interfaces 1 and 1' is also used for carrying the chromatograph effluent through 2-dimensional gas chromatograph 8. The importance of the inert auxiliary fluid becomes more significant in a multidimensional gas chromatograph having several interfaces, because the momentum initially supplied by the carrier gas may not be sufficient to carry the gas effluent all the way a detecting device. Regulators 36 and 36' of aperture means 5 and 5' respectively may be partially closed to provide above atmospheric pressure within junction means 10 and 10'. Inlet 12' of second interface 1' is connected to receive the chromatograph effluent from chromatographic column 64' of a second gas chromatograph generally indicated by numeral 2'. It should be noted that the liquid phases used in chromatographic columns 2 and 2' may differ in their ability to separate various components present in the sample introduced in gas chromatograph 2. Outlet 26' of second interface 1' is connected to orifice 50 of a detecting device generally indicated by numeral 3. Transfer member 24 and 24' of interface 1 and 1' respectively may be independently positioned by an actuation of driving means 40 and 40' respectively or transfer members 24 and 24' may be simultaneously positioned by an actuation by a single driving means, not shown in FIG. 5. If desired, interfaces 1 and 1' and GC columns 64 and 64' may be placed in the heated chambers maintained at desired temperatures.

Turning now to the operation of the embodiment as shown in FIG. 5 a sample containing various components is dissolved in a solvent, and then injected through injector 46 into gas chromatograph 2. The solvent containing the dissolved sample is then carried by the carrier gas. The gas chromatograph effluent exiting from chromatographic column 64 is fed through inlet 12 into first interface 1. A mixture from outlet 26 of interface 1 is fed into chromatographic column 64' of second chromatograph 2'. Thus by passing the gas chromatograph effluent through two interfaces interposed by two gas chromatographic columns, the components of the sample are separated even further into their constituents. It should be noted that the power of resolution may be enhanced even further by providing a series of interfaces alternated by a series of gas chromatographs.

The present invention will be further understood from the illustration of specific examples which follow. These examples are intended for illustrative purposes only and should not be construed as limitation upon the broadest aspects of the invention.

EXAMPLES

Figure 6:
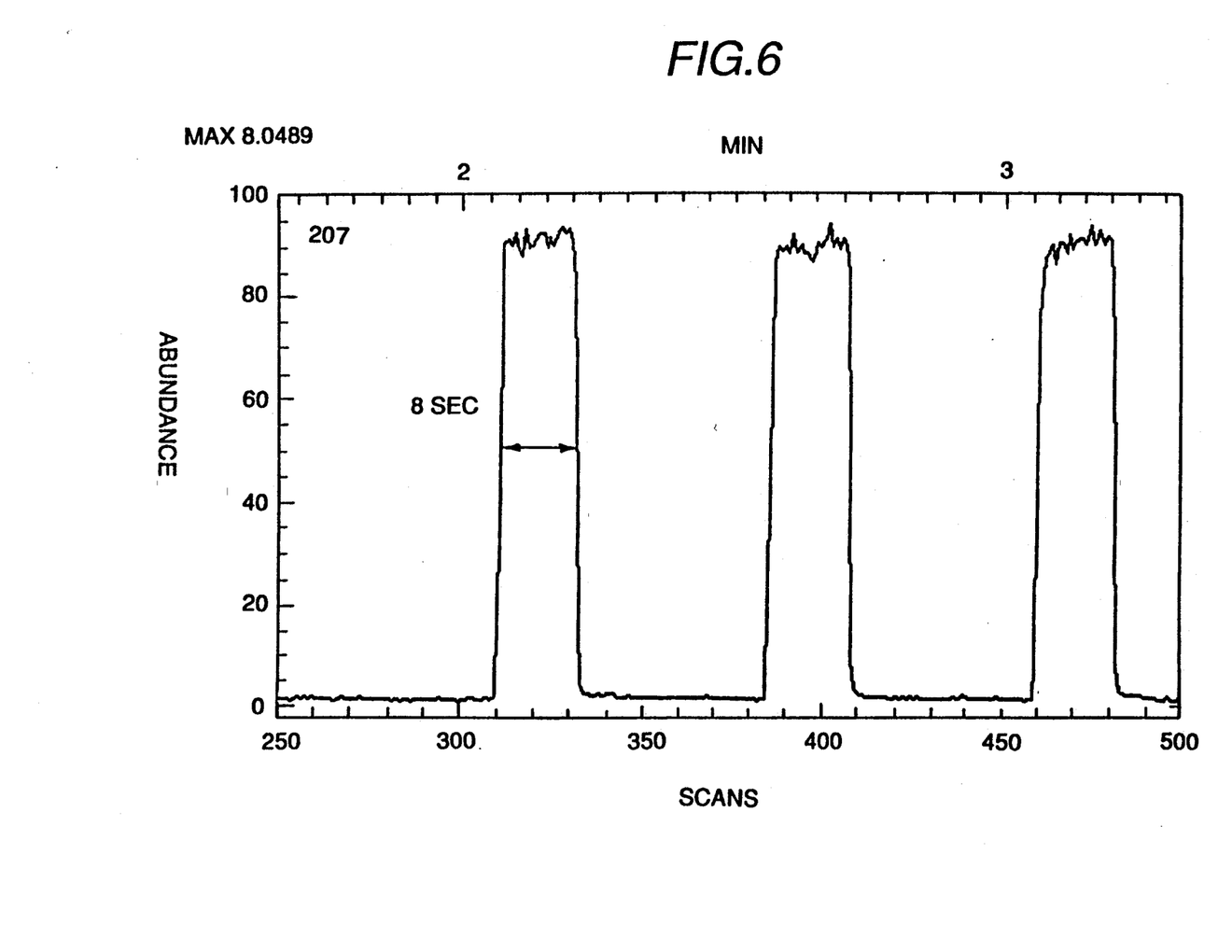
FIG. 6 is a scan showing switching responses of the apparatus of the preferred embodiment.
Figure 7:
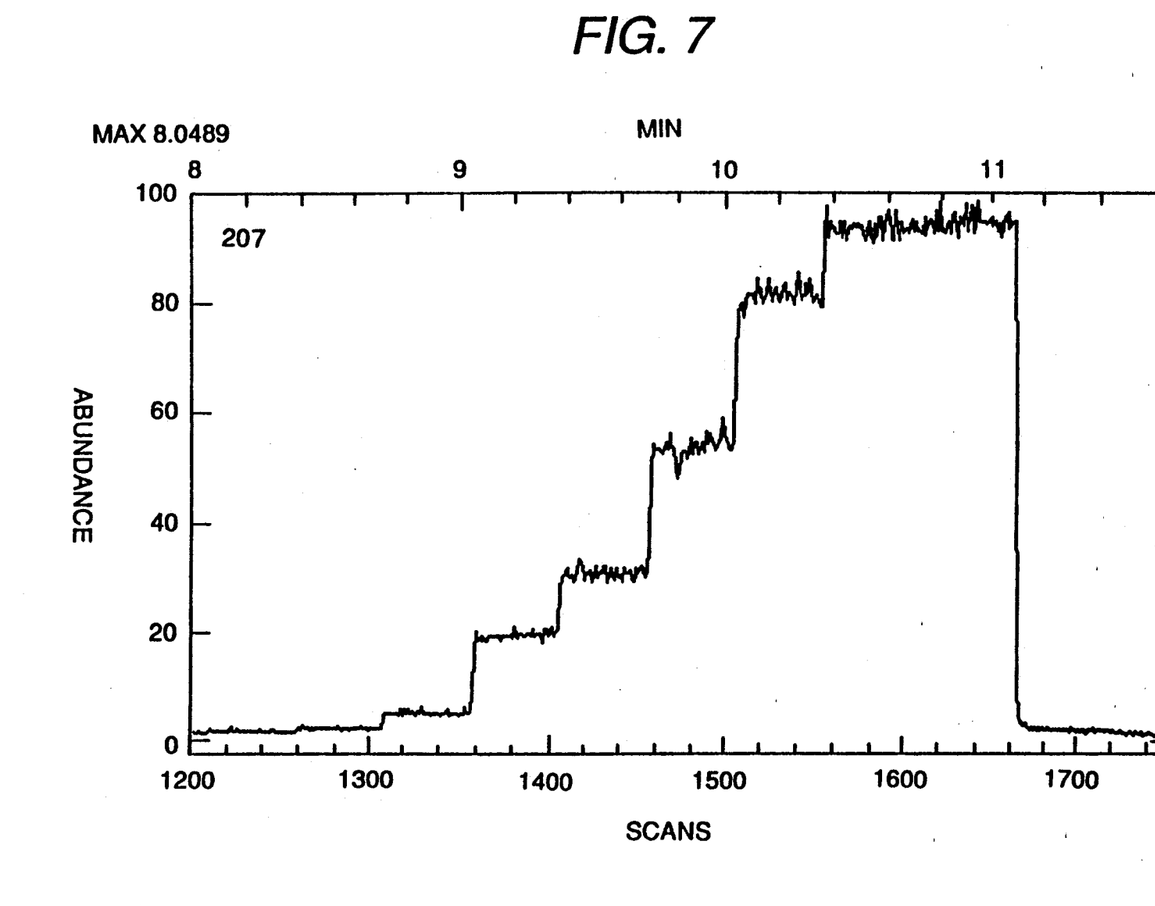
FIG. 7 is a scan showing incremental switching response of the apparatus of the preferred embodiment.

FIG. 6 represents a scan showing the on/off switching ability, the switching speed and the switching reproducibility of interface 1, shown in FIG. 2. FIG. 7 represents a scan showing the partial switching ability of interface 1 of FIG. 2 achieved through incremental positioning of transfer member 22 between first position 25 and second position 27. The GC effluent used for both the scans had a mass of 207 at a GC effluent flow of about 2 milliliters per minute and inert auxiliary fluid flow at about 2.5 milliliters per minute. The gas chromatograph was operated at about 300° C. The distance between first position 25 and second position 27 was about 2.0 millimeters.

While particular embodiments of the invention have been shown, it will be understood, of course, that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention.

What is claimed is:

1. Analytical apparatus comprising:
   at least one gas chromatograph;
   a detecting device; and
   an interface including a junction means connecting said gas chromatograph to said detecting device;
   said junction means comprising:
   a conduit having a first end and a second end;
   at least one inlet at said first end connected to said at least one chromatograph for receiving a chromatograph effluent;
   a supply means connected to said junction means through a port located at said second end for introducing an inert auxiliary fluid within said junction means to form a mixture comprising said effluent, said inert fluid or a combination thereof;
   an exhaust port located between said first and second ends and connected to an aperture means for controlling fluid pressure within said junction means;
   a bellows affixed to said conduit at said second end;
   an actuating lever having a driven end connected to said bellows and a driver end connected to a driver means for providing a reciprocal motion to at least one transfer member by actuation of said bellows by said driver means;
   said at least one transfer member including an outlet portion, perpendicular to said conduit, said outlet portion being connected to said detecting device for conveying said mixture to said detecting device, said transfer member being disposed partially within and having an inlet portion parallel to said conduit and being selectively positionable between a first position and a second position such that when said transfer member is in said first position said mixture is directed to said exhaust port and when said transfer member is in said second position said mixture is directed to said outlet; and
   said driver means directing said transfer member to said first position or to said second position.

2. Apparatus according to claim 1 wherein the detecting device is a mass spectrometer.

3. Apparatus according to claim 1 wherein said driver means is powered by electro-mechanical means controlled through a software program executed by computer means.

4. Apparatus according to claim 1 wherein said first position is proximal to said exhaust port, said second position is proximal to said first end and said outlet portion is sealably and flexibly coupled to said detecting device.

5. Apparatus according to claim 1 wherein said interface is of inert material.

6. Apparatus according to claim 1 wherein said aperture means is capable of adjustment to expose said junction means to varying pressures.

7. Apparatus according to claim 1 wherein said junction means has a plurality of said inlets connected to a plurality of said chromatographs.

8. Apparatus according to claim 1 wherein said transfer member is a capillary tube.

9. Apparatus according to claim 1 further comprising a heated chamber for enclosing and maintaining said detecting device and said interface at a desired temperature.

10. Analytical apparatus comprising:
    at least one gas chromatograph;
    a detecting device; and
    an interface including a junction means connecting said gas chromatograph to said detecting device;
    said junction means comprising:
    a manifold having a first end and a second end;

at least one inlet located between said first and second ends connected to said at least one chromatograph for receiving a chromatograph effluent;

at least one outlet located at said first end and connected to said detecting device for conveying a fluid mixture from said junction means to said detecting device;

an exhaust port located at said second end and connected to an aperture means for controlling fluid pressure within said manifold;

at least one transfer member including a supply means for introducing an inert auxiliary fluid into said junction means to form said fluid mixture comprising said effluent, said inert fluid or a combination thereof, said transfer member being disposed partially within said junction means and being selectively positionable between a first position and a second position such that when said transfer member is in said first position said mixture is directed to said exhaust port and when said transfer member is in said second position said mixture is directed to said outlet; and a driving means for directing said transfer member to said first position or to said second position.

11. Apparatus according to claim 10 wherein the detecting device is a mass spectrometer.

12. Apparatus according to claim 10 wherein said first position is proximal to said first end and said second position is proximal to said second end.

13. Apparatus according to claim 10 wherein said junction means is of inert material.

14. Apparatus according to claim 10 wherein said aperture means is capable of adjustment to expose said junction means to varying pressures.

15. Apparatus according to claim 10 wherein said transfer member is a capillary tube.

16. Apparatus according to claim 10 further comprising a heated chamber for enclosing and maintaining said detecting device and said interface at a desired temperature.

* * * * *